United States Patent [19]

Heefner et al.

[11] Patent Number: 5,231,007

[45] Date of Patent: Jul. 27, 1993

[54] EFFICIENT RIBOFLAVIN PRODUCTION WITH YEAST

[75] Inventors: Donald L. Heefner, Longmont; Annette Boyts, Golden; Linda Burdzinski, Louisville; Michael Yarus, Boulder, all of Colo.

[73] Assignee: Zeagen, Inc., Broomfield, Colo.

[21] Appl. No.: 746,208

[22] Filed: Aug. 15, 1991

Related U.S. Application Data

[63] Continuation of Ser. No. 251,943, Sep. 29, 1988, abandoned, which is a continuation of Ser. No. 811,243, Dec. 20, 1985, abandoned.

[51] Int. Cl.$^5$ .................. C12N 1/16; C12N 15/00; C12P 25/00
[52] U.S. Cl. .................................. 435/66; 435/255; 435/172.1; 435/921
[58] Field of Search ............... 435/66, 255, 921, 911, 435/944, 84, 85, 172.1, 86

[56] References Cited

U.S. PATENT DOCUMENTS

| | | | |
|---|---|---|---|
| 2,363,227 | 11/1944 | Burkholder | 435/66 |
| 2,424,003 | 7/1947 | Tanner et al. | 435/66 |
| 2,571,115 | 10/1951 | Davis | 195/79 |
| 3,900,368 | 8/1975 | Enei et al. | 435/66 |
| 4,172,764 | 10/1979 | Heslot et al. | 435/172.2 |

FOREIGN PATENT DOCUMENTS

| | | | |
|---|---|---|---|
| 0137226 | 4/1985 | European Pat. Off. | 435/66 |
| 0140707 | 8/1985 | European Pat. Off. | |
| 108767 | 10/1974 | Fed. Rep. of Germany | |

OTHER PUBLICATIONS

Garraway et al, "Fungal Nutrition and Physiology" 1984, Wiley and Sons pp. 184-187.
Schlee et al. "Biochemie und Physiologie der Flavinogenese in Mikroorganismen" *Pharmazie*, vol. 25, pp. 651-669 (1970).
Lodder, J. "The Yeasts" 1970, N. Holland Publishing Co.
Olczyk, C. 1978, *J. Pharmacol. Pharm* 30:83-88.
Demain (1972) Ann Rev. Microbiol 26:369-388.
Tanner et al. (1945) vol. 101, pp. 180-181 Science.
Harris, W. J. In Biotechnology, ed. Cheremisinoff, 1985, Technomic Public. Co., pp. 9-18.
T. W. Goodwin, Production and Biosynthesis of Riboflavin in Micro-Organisms (1959) 1:139-177 in *Process in Industrial Microbiology*.
Thomas G. Pridham; *Econ. Bot.* (1952) 6:185-205 "Microbial Synthesis of Riboflavin".
D. Perlman, *Economic Microbiology* (1978) 2:310-317, "Primary Products Metabolism".
Levine et al., Industrial and Engineering Chemistry (1949) 41:165.
Matsui et al., Agric. Biol. Chem. (1979) 43:394.
Pickering et al., Heredity (1972) 28:275-276.
A. A. Imshenetskii et al., *Chemical Abstracts*, (1977), 86: 272.
B. Sikyta; Methods in Industrial Microbiology; (1983); pp. 220-229.

*Primary Examiner*—Irene Marx
*Attorney, Agent, or Firm*—Sheridan Ross & McIntosh

[57] ABSTRACT

A method of systematically generating and isolating highly flavinogenic strains of *Candida famata*. The strains *Candida famata* GA18Y8-6#2 dgr and *Candida famata* GA18Y8-6#2#11 have been developed and produce yields of ca. 7.0 to 7.5 grams per liter per 6 days. The method includes a combination of iterative mutagenizing steps and protoplast fusion steps performed on the parent strain and the descendant strains which are selected following each step according to a screening protocol.

4 Claims, No Drawings

EFFICIENT RIBOFLAVIN PRODUCTION WITH YEAST

This is a continuation of co-pending application Ser. No. 07/251,943, now abandoned, filed on Sep. 29, 1988, which is a continuation of application Ser. No. 06/811,243, now abandoned, filed Dec. 20, 1985.

BACKGROUND OF THE INVENTION

1. Field of the Invention

The present invention relates to the generation and isolation of flavinogenic strains of *Candida famata* for the production of riboflavin.

Riboflavin, most commonly known as vitamin $B_2$, an enzyme cofactor is found to some degree in virtually all naturally occurring foods. It is widely used in pharmaceuticals, food-enrichment, and feed supplements.

Riboflavin has been commercially produced by fermentation. Most commercially produced riboflavin is consumed as a crude concentrate for enriching animal feed. Riboflavin also finds use for human consumption. The present invention is concerned with the development of *Candida famata* strains for the efficient and economic production of riboflavin.

2. Brief Description of the Relevant Literature

Varieties of Candida yeasts are attractive as flavinogenic organisms because they grow rapidly on a simple, well known medium. P. R. Burkholder, *Proc. Nat. Acad. Sci., U.S.A.*, (1943) 29:166.

*Candida famata* has been studied for a number of years for its flavinogenic capacities. See, e.g., Enari and Kauppinen, *Acta. Chem. Scand.* (1961) 15:1513. In particular, the inhibitory effect of iron and trace elements on riboflavin production has been investigated. Tanner et al., *Science* (1945) 101:180. So far, riboflavin production by *C. famata* has proven to be variable. Early pilot plant fermentations using simple non-sterilized culture mediums gave riboflavin yields of 325 mg/liter. Levine, H., et al., *Industrial and Engineering Chemistry* (1949) 41:1665.

Certain varieties of Candida yeasts have been known to produce substantial amounts of riboflavin. For example, a modification employing *Candida intermedia var A*, a newly isolated microorganism assimilating lactose and ethanol, has ben disclosed in Japanese Patent No. 73/19,958 and yields reported of 49.2 mg riboflavin per liter. Candida T-3 also produces riboflavin from methanol, as disclosed in Japanese Patent No. 76/19,187. See also, EPA 0 137 226 for disclosure of *Candida robusta* for riboflavin production.

SUMMARY OF THE INVENTION

Enhanced riboflavin production is achieved employing a mutated Candida strain. Starting with a riboflavin producing Candida strain, the strain is subjected to a regimen of chemical and/or physical mutagenesis and protoplast fusions of mutagenized strains to produce a strain having efficient production of riboflavin and reduced sensitivity to iron and inhibitors of purine and riboflavin biosynthesis. A mutant, dgr, was also isolated and exhibited enhanced flavinogenic activity.

DESCRIPTION OF THE SPECIFIC EMBODIMENTS

Methods and organisms are provided for enhanced production of riboflavin. A riboflavin-producing Candida strain is selected, subjected to a course of mutagenesis, mutagenized strains screened as to a variety of traits associated with flavinogenesis, desirable mutants are fused, the fusion progeny screened and subjected to further mutagenesis to provide strains producing riboflavin with high efficiency at stable and reproducible levels, with reduced resistance to repression of the $B_2$ pathway by resistance to catabolite repression by glucose, resistance to inhibition of the purine pathway by adenosine monophosphate, and the adenine antimetabolite 4-amino pyrazolo(3,4-d)pyrimidine (APP).

Mutants are selected where the riboflavin synthesis is no longer as sensitive to or insensitive to flavin adenine dinucleotide and/or adenosine monophosphate regulation, where phosphoribosylpyrophosphate amidotransferase has reduced sensitivity to regulation by adenine and adenosine, and where the mutant is substantially insensitive to APP. By insensitive or deregulated it is intended that production rates of the mutant are unaffected at concentrations in a nutrient medium which would reduce production rates by at least fifty percent. In addition, the mutant is substantially resistant to catabolite repression as evidenced by lack of response to deoxyglucose at levels which repress respiration in wild-type *Candida famata*.

The method involves a course of mutagenesis and fusion, where at each stage, screening is carried out as to enhancement of riboflavin production, associated with particular characteristics related to the purine and riboflavin metabolic pathway. Desirably, the mutants provide for high riboflavin yields in the presence of an amino acid source in the nutrient medium.

The mutagenesis is carried out employing either physical or chemical mutagens with the organisms being grown in a medium stimulating flavinogenesis. Additives which support flavinogenesis include glycine at levels of from about 0.1 to 0.3%, particularly about 0.2 to 0.25%. In addition, trace amounts of cobalt and zinc ions are desirable. The cobalt concentration will generally be in the range of about 0.5 to $2\mu g/ml$, preferably about 1 $\mu g/ml$, while the zinc concentration will generally be about 5 to 25 $\mu g/ml$, usually about 5 to 15 $\mu g/ml$. Optionally $Fe^{+3}$ may be present in from about $0.1-0.3\mu g/ml$. In addition, a carbon source is employed, most sugars being acceptable, e.g., glucose, sucrose, fructose, galactose, etc. With sucrose, the concentration will be generally from about 1 to 8%, preferably about 6%. Comparable concentrations may be used with the other sugars.

At various stages of the mutagenesis and fusion regimen, the mutants will be screened on either defined medium (flavinogenesis-stimulating and lacking amino acids except for glycine) or complex medium (rich nutrient medium containing amino acids), which may contain one or more organic compounds which inhibit one or more enzymes in the purine biosynthesis pathway. Of particular interest is resistance to AMP and APP. In addition, intermediate mutants may be selected on the basis of deregulation of the purine biosynthesis pathway, particularly in the early half of the pathway, more particularly in the first three or four steps.

The resulting mutagen will have at least a 20% increase in riboflavin production over the immediately preceding parent strain and the final mutant will have at least bout a 5-fold, preferably at least about a 10-fold, increase in riboflavin production over the original parent strain and have a reduced sensitivity to iron.

Mutagenesis may be carried out either by physical or chemical means, such as irradiation with ultraviolet light or X-rays, or by chemical mutagens, such as nitroso compounds, e.g., nitrosoguanidine, alkylating compounds, e.g., ethyl methanesulfonate, mustard compounds, hydrazine, nitrous acid, or the like. The particular technique for mutageneis is not critical, and conventional techniques may be employed. The conditions for mutagenesis will generally result in a reduction in viability.

The resultant mutant strains may then be screened for resistance to APP or deoxyglucose, loss of regulation in the purine pathway, or loss of inhibition of $B_2$ synthesis by iron, AMP and/or a complex medium (includes amino acids, individually or as peptides).

For fusion, protoplasts are employed where the cell wall is removed. A mixture of zymolase, particularly from *Arthrobacter luteus*, and $\beta$-glucuronidase, particularly from *Helix pomatia*, is found to be effective. Desirably, the mutant strains are selected as auxotrophs, where each of the strains employed lacks one or more metabolic pathways for production of one or more amino acids. The heterokaryons which are formed may then be selected as prototrophic and screened for enhanced riboflavin production.

At each stage of mutagenesis or fusion, at least a 20%, preferably at least about a 50%, increase in riboflavin production is observed over the original parent. The number of stages will be at least three, and preferably not more than ten, preferably not more than about eight, of strain modifications, involving combinations of mutagenesis and fusion.

The mutagenesis may be carried out in any medium, e.g. a flavinogenesis-stimulating medium, and the resulting viable mutagens screened in a flavinogenesis-stimulating medium. In accordance with the subject invention, mutants are obtained employing different mutagenic agents. One strain is selected from each mutagenesis, one based on enhanced riboflavin production in the presence of adenosine monophosphate and the other strain selected based on enhanced riboflavin production and lack of regulation in an early stage of the purine biosynthesis synthetic pathway.

Each of the strains is then marked for amino acid auxotrophy by determining colonies which do not grow on medium lacking a particular amino acid and would grow on medium containing the particular amino acid. In the subject invention, the amino acids selected for were histidine and methionine. Auxotrophs of each of the two strains are treated with saccharidases, particularly a mixture of zymolase and $\beta$-glucuronidase, to prepare protoplasts which are fused in the presence of a nonionic detergent, followed by transfer to a nutrient medium lacking any amino acid source. The resulting prototrophs are examined for riboflavin production and those having enhanced riboflavin production are selected.

The fused cells are then subjected to a further mutagenesis regimen, in this instance chemical mutagenesis, and strains selected for enhanced riboflavin production.

Two strains were isolated of particular interest, designated GA18Y8-6#2 dgr, ATCC Accession No. 20756, and GA18Y8-6#2#11, ATCC Accession No. 20755. In defined medium, these strains produce greater than about 5 grams riboflavin per liter in 6 days, usually greater than about 7 grams per liter in 6 days, employing 5ml of an exponentially growing culture as an inoculum into 50 ml of the defined medium. (The medium is 4B+0.2% glycine+Co+Zn+Fe+10% YMG (2% glucose, yeast extract, peptone and malt extract). Every 24 hr, the culture is fed 2 ml of 10X 4B+glycine+Co+Zn.)

EXPERIMENTAL

Mutagenesis

Mutants were obtained by mutagenesis, using either methyl N'-nitrosoguanidine (NTG) or ultraviolet light. The initial parent strain of *C. famata* was mutagenized using NTG. The mutant GR3 wa obtained using this method on a first culture of the initial parent strain of *C. famata* NRRL Y245. 20 ml of an overnight culture of the parent strain was washed and suspended in 20 ml of 4B medium ("defined medium") with 0.2% glycine added. (Burkholder, *Proc. Natl. Acad. Sci. USA* (1943) 29:166.) (4B medium plus glycine is prepared by dissolving in 1L water 0.5 g $KH_2PO_4$; 0.2 g $MgSO_4.7H_2O$, 1.84 g urea, 60 g sucrose, 1 $\mu$g D-biotin, 20$\mu$g $H_3BO_4$, 20 $\mu$g $MnSO_4$, 140 $\mu$g $ZnSO_4$, 20 $\mu$g $CuSO_4$, 20 $\mu$g $Na_2MoO_4$ and 2.3 g glycine. When cobalt and zinc are indicated 1 $\mu$g $CoCl_2$ and 10 mg $ZnCl_2$ are added.) NTG (10 m9/ml) in DMSO was added to the culture medium to a final concentration of 100 $\mu$g/ml. The culture was stirred at 30° C. for one hour before harvesting and washing.

This treatment resulted in a logarithmic decrease in viable cells.

Mutagenesis was also induced using ultraviolet radiation. The mutant A22 was obtained using this method. A second overnight culture of the parent strain, grown in 4B medium (See, Levine, H., et al., *Industrial and Chemical Engineering* (1949) 41:1666) with 0.2% glycine, was washed and suspended in an equal volume (35 ml) of the same medium in a plastic petri dish. The medium was then stirred and exposed to ultraviolet radiation of 200-290 nm. This level of irradiation reduced the viable number of cells to 10% of the starting culture. The cells were then plated on defined medium containing 25 mM 5'-AMP Mutagenesis, plating and incubation were done in the dark. Mutant A22 was found to produce riboflavin in the presence of 5'-AMP, an inhibitor of flavinogenesis.

Screening Protocol for GR3 Strain

The above-described NTG mutagenized culture was washed twice in 20 ml of saline solution and suspended in the same volume of YMG medium (complex medium). The components of YMG medium are per L, 3 g yeast extract, 3 g malt extract, 5 g peptone, and 100 ml of a carbon source, e.g. glucose, (2%) immediately prior to use. The culture was then incubated with shaking at 30° C. for 48 hours. The cells were then harvested, washed three times in 20 ml of saline solution and resuspended in 4B medium without urea or glycine. After overnight nitrogen starvation, the cells were harvested and suspended in a yeast nitrogen base medium without amino acids and containing 2% glucose. The culture was then incubated for six hours.

A fresh nystatin solution was prepared by dissolving 1 mg of nystatin in 1 ml of ethanol, followed by dilution to 10 ml with distilled water. The nystatin solution was then added to a final concentration of 20 $\mu$g/ml to kill vegetative cells.

Following the nystatin treatment, the viable cells were diluted to $10^{-4}$-$10^{-5}$ in saline and 0.1 ml samples were plated onto YMG plates (20 g agar/L of YMG medium). After two days of incubation, the colonies on the YMG plates were replica-plated onto defined medium.

Colonies which grew on the complex medium but not on the defined medium were then streaked onto a defined medium containing adenine at 30 μg/ml. One colony was detected which grew on minimal medium as a white colony, and a pinkish-red colony on the minimal medium with adenine. This isolate, named GR3, was found to produce red colonies in the presence of 20–50 μg/ml adenine and white colonies in the presence of 0 or 100 μg/ml adenine. The red color of the colonies was attributed to the accumulation of P-ribosylaminoimidazole carboxylate (CAIR) and/or P-ribosylaminoimidazole (AIR). It was concluded that GR3 was a mutant defective in the regulation of the first step in the purine pathway. In this GR3 mutant, regulation at the first step is apparently defective because even in the presence of 20–50 μg/ml adenine, purine intermediates accumulated even though the mutant is not auxotrophic for purines.

Fusions

The GA18 strain was obtained by protoplast fusion of the mutant strains A22 and GR3. Following nystatin treatment as described above, each of the strains diluted in saline ($10^4$–$10^{-5}$) were plated onto complex medium. After two days incubation, the cells were replica-plated onto 4B medium. Colonies which did not grow on 4B were then streaked onto 4B supplemented either with histidine or methionine at 30 μg/ml. Cells which did not grow on the defined medium but which did grow on the medium supplemented with either amino acid were presumed to be auxotrophs. In this manner, a histidine auxotroph of A22 (A22 His$^-$) and a methionine auxotroph of GR3 (GR3 Met$^-$) were obtained.

To carry out the fusions, 48 hour cultures of A22 His$^-$ and GR3 Met$^-$ were grown on 4B medium plus glycine, harvested, washed once in 20 ml of distilled water, and suspended in 20 ml of a 1 M sorbitol, 25 mM EDTA and 50 mM dithiothreitol solution. The suspensions were incubated for 20 min at 30° C. with occasional gentle shaking. The cells were then harvested, washed once in 20 ml of 2 M sorbitol, and each auxotroph was suspended in 20 ml of a 1.5 M sorbitol, 0.1 M sodium citrate, pH 5.8, and 0.01 M EDTA solution. To each suspension was then added 0.2 ml of β-glucuronidase (Type H-2, from *Helix pomatia*, 100,000 units/ml, Sigma) and 20 mg of zymolase 100T (Miles Laboratory). The suspensions were incubated at room temperature for 45 min. During this time, the normally elongated cells took on a rounded spherical form indicating digestion of the cell walls.

After the enzyme treatment, the protoplasts of each auxotroph were harvested by low speed centrifugation (5000×g), washed two times in 10 ml 2 M sorbitol; once in 10 ml of 1.5 M sorbitol, 10 mM CaCl$_2$, and 10 mM Tris HCl pH 7.5, and then suspended in 0.5 ml of the same. To fuse the protoplasts, 0.1 ml samples of each auxotroph were mixed, and 0.1 ml of a solution of 20% PEG (Sigma, approximate molecular weight 6000), 10 mM CaCl$_2$, and 10 mM Tris HCl pH 7.4 was added.

The mixture was incubated at room temperature for 20 min with occasional shaking. The cells were then centrifuged, washed one time in 10 ml of yeast nitrogen base medium without amino acids with 2% glucose and 1.5 M sorbitol, and suspended in 0.5 ml of the same. Samples of about 0.1 ml, were then added to 7 ml of the same medium containing 2.0% agar (at about 55° C.) and overlaid onto the same medium. Most of the solutions used in this procedure can be found in *Methods in Yeast Genetics*, Cold Spring Harbor Laboratory, Cold Spring Harbor, N.Y., 1981, p. 115. In the absence of amino acids, neither auxotroph will grow (there being a very low revertant frequency). Colonies which formed after 6–9 days incubation at 30° C. contained prototrophs which arose as a result of genetic exchange. Prototrophs resulting from the fusion procedure occurred at a frequency of about one in $10^3$ survivors of the polyethylene glycol treatment. The colonies were examined under low magnification, and those colonies containing riboflavin crystals were restreaked and examined for riboflavin production in the defined medium. One colony was designated GA18.

Second Mutation and Screening Yields GA18Y8-6#2

The strain GA18Y8-6#2 was obtained by mutagenizing a 48 hour parent culture of GA18 with the NTG method previously described. Following mutagenesis, the cells were washed, diluted to $10^{-4}$ and $10^{-5}$, and 0.1 ml plated on YMG. GA18 did not form yellow colonies, that is, colonies with a high riboflavin content on the YMG medium. This was attributed to repression of flavinogenesis by iron or some organic component in the medium. After a one week incubation period, a few yellow colonies were noted, picked and restreaked several times on YMG to purify the strain. The purified strain was designated GA18Y8-6#2.

The Mutated Strains

The strains which presently are the most efficient riboflavin producers ar identified as *Candida famata* GA18Y8-6#2 dgr, having A.T.C.C. Accession No. 20756, and *Candida famata* GA18Y8-6#2#11, having A.T.C.C. Accession No. 20755. These strains were derived from the above-described experimental method.

GA18Y8-6#2 dgr produces 7.0 to 7.5 grams riboflavin per liter per 6 days using 5 ml of an exponentially growing culture as an inoculum into 50 ml of the defined medium described previously and supplemented with 0.2μg FeCl$_3$ and 10% YMG. This strain was obtained by NTG mutagenesis of the parent strain GA18Y8-6#2. Deoxyglucose is an analog of glucose and strongly inhibits cell growth when sucrose is used as a carbon source. Yellow colonies resistant to deoxyglucose were picked, purified by restreaking onto 4B plus glycine and deoxyglucose and tested for flavinogenesis. The mutagenized cells were plated onto 4B plus glycine medium containing 750 μg/ml 2-deoxyglucose. *Candida famata* GA18Y8-6#2 dgr was selected from the purified colonies.

GA18Y8-6#2#11 also produces 7.0–7.5 grams riboflavin per liter per 6 days using the same conditions as described previously for GA18Y8-6#2 dgr. This strain was obtained also by NTG mutagenesis of the parent strain GA18Y8-6#2. Following mutagenesis, the 20 ml of mutagenized culture was washed twice in 20 ml of distilled water, then suspended in 20 ml of YMG+FeCl$_3$ (2 μg/ml) +AMP (40 mM)+aminopyrazolopyrimidine, APP (500 μg/ml). This medium resulted in the selection of APP resistant colonies. This culture was incubated overnight, with periodic shaking, at 30° C. The cells were then harvested, washed twice in 20 ml of distilled water, and plated onto YMG+FeCl$_3$ (2 μg/ml)+APP (1 mg/ml)+AMP (40 mM) and incubated at 30° C. for a week. At the end of this time, the plates were inspected, and the yellow-orange colonies picked and examined for flavinogenesis. GA18Y8-6#2#11 was obtained from the purified colonies.

High riboflavin yields from the above strains were obtained with 50 ml of a growth medium in a 500 ml baffled growth flask. The growth medium consisted of 10% YMG + 90% 4B + glycine + Co + Zn + FeCl$_3$ (0.2 µg/ml). Optimal riboflavin production by derivatives of GA18 occurs in the presence of FeCl$_3$ at 0.2 µg/ml. In the wild type *C. famata*, FeCl$_3$ at 0.2 µg/ml represses riboflavin synthesis. The cultures were fed 2 ml of a 10×4B + glycine solution every 24 hours.

Further enhancement of riboflavin production and iron insensitivity may be achieved by repetition of the mutagenesis, selection and fusion procedures described above.

In accordance with the subject invention inefficient riboflavin producing strains of Candida can be mutated so as to stably produce high levels of riboflavin with efficient utilization of nutrients and improved resistance to iron repression of flavinogenesis.

The foregoing is a complete description of the invention, but is not intended to limit the scope of the invention, except as stated in the appended claims.

What is claimed is:

1. A strain having all of the identifying characteristics of *Candida famata* ATCC Accession No. 20755, or a mutant thereof, wherein said mutant produces at least about 5 grams of riboflavin per liter of fermentation medium in six days.

2. A strain having all of the identifying characteristics of *Candida famata* ATCC Accession No. 20756, or a mutant thereof, wherein said mutant produces at least about 5 grams of riboflavin per liter of fermentation medium in six days.

3. A method for using a *Candida famata* microorganism to produce riboflavin comprising:
   a) culturing said microorganism in an aqueous nutrient medium, wherein said microorganism has all of the identifying characteristics of *Candida famata* ATCC Accession No. 20755, or a mutant thereof capable of producing at least about 5 grams of riboflavin per liter of fermentation medium in six days upon inoculating an exponentially growing culture of said microorganism or said mutant into a fermentation broth at a ratio of said culture to said fermentation broth of about 1:10 and wherein said fermentation broth comprises 4B medium, from about 0.1 µg/ml to about 0.3 µg/ml of iron, about 10 percent by volume of YMG, and an amount of glycine, cobalt and zinc effective to stimulate flavinogenesis; and
   b) recovering riboflavin produced by said microorganism.

4. A method for using a *Candida famata* microorganism to produce riboflavin comprising:
   a) culturing said microorganism in an aqueous nutrient medium, wherein said microorganism has all of the identifying characteristics of *Candida famata* ATCC Accession No. 20756, or a mutant thereof capable of producing at least about 5 grams of riboflavin per liter of fermentation medium in six days upon inoculating an exponentially growing culture of said microorganism or said mutant into a fermentation broth at a ratio of said culture to said fermentation broth of about 1:10 and wherein said fermentation broth comprises 4B medium, from about 0.1 µg/ml to about 0.3 µg/ml of iron, about 10 percent by volume of YMG, and an amount of glycine, cobalt and zinc effective to stimulate flavinogenesis; and
   b) recovering riboflavin produced by said microorganism.

* * * * *